United States Patent [19]

Leaf et al.

[11] Patent Number: 5,576,349
[45] Date of Patent: Nov. 19, 1996

[54] RETIONOIC ACID TREATMENT OF CARDIAC ARRHYTHMIA

[75] Inventors: Alexander Leaf, Winchester; Jing X. Kang, North Andover, both of Mass.

[73] Assignee: The General Hospital Corporation, Boston, Mass.

[21] Appl. No.: 565,160

[22] Filed: Nov. 30, 1995

[51] Int. Cl.$^6$ .......................... A61K 31/20; A61K 31/07
[52] U.S. Cl. ............................................ 514/559; 514/725
[58] Field of Search ...................... 514/559, 729

[56] References Cited

U.S. PATENT DOCUMENTS 4,678,808  7/1987  Ward et al. ............................ 514/560
5,310,554  5/1994  Haigh ..................................... 424/439

FOREIGN PATENT DOCUMENTS 4-29928  1/1992  Japan .

OTHER PUBLICATIONS

Airaksinen et al., "Association between Silent Coronary Artery Disease, Diabetes, and Autonomic Neuropathy. Fact or Fallacy?" *Diabetes Care* (1992) 15:288–292.

Aronow, "Prevalence of Presenting Symptoms of Recognized Acute Myocardial Infarction and of Unrecognized Healed Myocardial Infarction in Elderly Patients," *Am. J. Cardiol.* (1987) 60:1182.

Billman, "Effect of Calcium Channel Antagonists on Cocaine–Induced Malignant Arrhytmias: Protection against Ventricular Fibrillation," *J. Pharm. and Exp. Ther.* 266:407–416 (1993).

Billman, "Effect of Calcium Channel Antagonists on Suceptibility to Sudden Cardiac Death: Protection from Ventricular Fibrillation," *J. Pharm. Expt. Therap.* (1989) 248:1334–1342.

Billman et al., "Elevated Myocardial Calcium and its Role in Sudden Cardiac Death," *FASB* 5:2586–92 (1991).

Billman, "Ro 40–5967, a Novel Calcium Channel Antagonist, Protects Against Ventricular Fibrillation," *Eur. J. Pharmacol.* (1992) 229:179–187.

Billman, "The Calcium Channel Antagonist, Flunarizine, Protects Against Ventricular Fibrillation," *Eur. J. Pharmacol.* (1992) 212:231–235.

Hallaq et al., "Protective effect of eicosapentaenoic acid on ouabain toxicity in neonatal rat cardiac myocytes," *Proc. Natl. Acad. Sci. USA* (1990) 87:7834–7838.

Hallaq et al., "Modulation of Dihydropyridine–sensitive Calcium Channels in Heart Cells by Fish Oil Fatty Cells," *Proc. Natl. Acad. Sci. USA* (1992) 89(5):1760–1764

Juan et al., "Effect of exogenous 5, 8, 11, 14, 17–eicosapentaenoic acid on cardiac anaphylaxis," *Br. J. Pharmac.* (1987) 90:315–325.

Kamp et al., "pH gradients across phospholipid membranes caused by fast flip–flop of un–ionized fatty acids," *Proc. Natl. Acad. Sci. USA* 89:11367–11370 (1992).

Kang et al., "Free long–chain, polyunsaturated fatty acids reduce membrane electrical excitability in neonatal rat cardiac myocytes," *Proc. Natl. Acad. Sci. USA* 92:3997–4001 (1995).

Kang et al., "Effects of long–chain polyunsaturated fatty acids on the contraction of neonatal rat cardiac myocytes," *Proc. Natl. Acad. Sci. USA* 91:9886–9890 (1994).

Leaf et al., "Cardiovascular Effects of n–3 Fatty Acids," *New England Journal of Medicine* (1988) 318:549–557.

Leaf, "Cardiovascular Effects of Fish Oils: Beyond the Platelet," *Circulation* (1990) 82:624–628.

McLennan et al., "Dietary Fish Oil Prevents Ventricular Fibrillation Following Coronary Artery Occlusion and Reperfusion," *American Heart Journal* (1988) 116:709–717.

McLennan et al., "Influence of Dietary Lipids on Arrhythmias and Infarction after Coronary Artery Ligation in Rats," *Can. J. Physiol. Pharmacol.* (1985) 63:1411–1417.

Makita et al., "Successful Management of Life–Threatening Ventricular Arrhythmias with Propafenone in a Hemodialysis Patient," *Current Therapeutic Research* (1991) 49:954–960.

Steen et al., "Myocardial Reinfarction After Anesthesia and Surgery," *JAMA* (1978) 239(24):2566–2570.

Xiao et al., "Blocking effects of polyunsaturated fatty acids in Na+ channels of neonatal rat ventricular myocytes," *Proc. Nat. Acad. Sci..*, 92:1000–11004 (1995).

Yamashita et al., "Effect of Eicosapentaenoic and Docosahexaenoic Acid on Natural Killer Cell Activity in Human Peripheral Blood Lymphocytes," *Clinical Immunology and Imunopathology* (1991) 59:335–345.

Yamazaki et al., "Changes in fatty acid composition in rat blood and organs after infusion of docosahexaenoic acid ethyl ester$^{1-3}$," *Am. J. Clin. Nutr.* (1991) 53:620–627.

*Primary Examiner*—Raymond Henley, III
*Attorney, Agent, or Firm*—Fish & Richardson P.C.

[57] ABSTRACT

Disclosed is a method for terminating an existing potentially lethal cardiac arrhythmia, or preventing an imminent potentially lethal cardiac arrhythmia. The method involves administration of all-trans-retinoic acid or an antiarrhythmically active analog. Antiarrhythmic effects of all-trans-retinoic acid occur within minutes.

13 Claims, 2 Drawing Sheets

RETIONOIC ACID TREATMENT OF CARDIAC ARRHYTHMIA

STATEMENT AS TO FEDERALLY SPONSORED RESEARCH

Work on this invention was supported, in part, with funds from the United States government (National Institutes of Health, National Institute of Diabetes and Digestive and Kidney Diseases Grant R01-DK 38165). The government therefore has certain rights in the invention.

FIELD OF THE INVENTION

This invention relates to cardiac arrhythmia and methods of cardiac treatment.

BACKGROUND OF THE INVENTION

Cardiac arrhythmias, such as ventricular fibrillation and ventricular tachycardia, can lead to sudden death, i.e., within minutes. Potentially lethal cardiac arrhythmias occur typically in patients experiencing a myocardial infarction or other conditions that cause ischemia in cardiac tissue. The high incidence of recurrent ventricular fibrillation and resulting sudden death indicates a need for effective treatment methods to prevent life-threatening arrhythmias.

SUMMARY OF THE INVENTION

We have discovered that all-trans-retinoic acid induces a marked and reversible reduction in the beating rate of isolated neonatal rat cardiac myocytes, within 2 to 5 minutes. In addition, we have discovered that all-trans-retinoic acid terminates and prevents artificially induced arrhythmias in the isolated myocytes. We have further discovered that in a whole animal model of arrhythmia, intravenous infusion of all-trans-retinoic acid significantly reduces the incidence and the severity of ventricular tachycardia and ventricular fibrillation.

Based on these discoveries, the invention features a method for terminating an existing potentially lethal cardiac arrhythmia, or preventing an imminent potentially lethal cardiac arrhythmia. The method includes administering a composition containing an effective amount of antiarrhythmic compound defined by the formula:

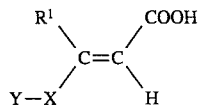

wherein X is selected from the group consisting of:

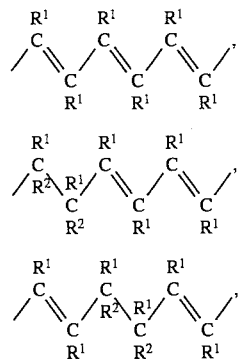

-continued
and

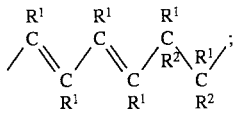

Y is selected from the group consisting of:

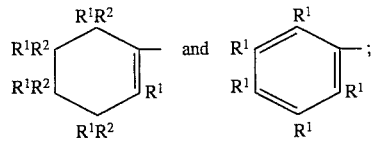

$R^1$ is selected from the group consisting of H, methyl, and ethyl; and $R^2$ is selected from the group consisting of H, methyl, and ethyl. In a preferred embodiment of the invention, the antiarrhythmic compound administered is all-trans-retinoic acid.

The method of this invention is particularly useful where the potentially lethal cardiac arrythmia to be prevented or terminated is a ventricular fibrillation or ventricular tachycardia.

In the method of this invention, the amount of antiarrhythmic compound administered is preferably between 2 and 1,000 mg per kg total body weight. More preferably, the amount of antiarrhythmic compound administered is between 10 and 400 mg per kg total body weight. Preferably, the composition containing the antiarrhythmic compound is administered by intravenous infusion. Alternatively, the composition can be administered by bolus injection. The bolus injection can be intracardial.

In a preferred embodiment of the invention, the composition administered contains a transport protein suitable for serum transport of the antiarrythmic compound. A suitable transport protein is human serum albumin. When human serum albumin is used as a transport protein, the molar ratio of the antiarrhythmic compound to the human serum albumin is from 1 to 7. Preferably, the molar ratio is approximately 5.

As used herein, "active analog of retinoic acid" means any antiarrhythmic compound defined by the formula:

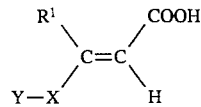

wherein X is selected from the group consisting of:

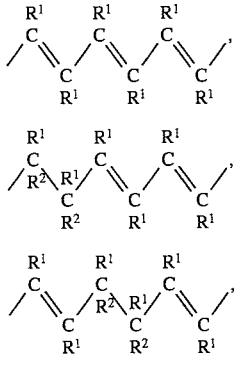

and

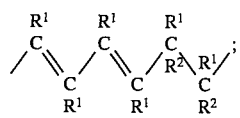

Y is selected from the group consisting of:

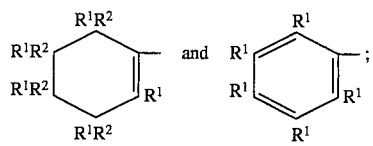

$R^1$ is selected from the group consisting of H, methyl, and ethyl; and $R^2$ is selected from the group consisting of H, methyl, and ethyl.

As used herein, "bolus injection" means the administration of a solution or emulsion, typically with a syringe and needle, directly into a selected site, so that the total volume of the solution or emulsion enters the selected site rapidly, e.g., within seconds.

As used herein, "intravenous infusion" means gradual introduction of a solution or emulsion directly into a vein, e.g., the cephalic or median basilic vein of the arm, over an extended period of time. The extended period of time is typically at least 30 minutes.

As used herein, "ischemia" means local reduction in blood flow due to mechanical obstruction.

As used herein, "myocardial infarction" means a sudden insufficiency of blood flow to the heart muscle, or some portion of the heart muscle.

As used herein, "potentially lethal cardiac arrhythmia" means a cardiac arrhythmia so prominent or severe that it causes a life-threatening interference with the normal pumping action of the heart. Examples of a potentially lethal cardiac arrhythmias include, but are not limited to, ventricular tachyarrhythmia, ventricular fibrillation, and ventricular bradyarrhythmia.

As used herein, "retinoic acid" means all-trans-retinoic acid, unless otherwise indicated.

As used herein, "ventricular fibrillation" means a ventricular tachyarrhythmia characterized by rapid, tremulous and ineffectual contractions of the ventricles. Ventricular fibrillation may result from mechanical injury to the heart, occlusion of coronary vessels, certain drugs (e.g., digitalis, cocaine, or chloroform), anaphylactic reactions, electrical stimulation, or electrolyte imbalance.

As used herein, "ventricular tachyarrhythmia" means any disturbance of ventricular rhythm, regular or irregular, resulting in a rate of over 100 beats per minute.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present application (or issued patent), including definitions, will control. In addition, the materials, methods, and examples are illustrative only and not intended to be limiting.

Other features and advantages of the invention will be apparent from the following description of the preferred embodiments thereof, and from the claims.

DETAILED DESCRIPTION

Figure 1A:
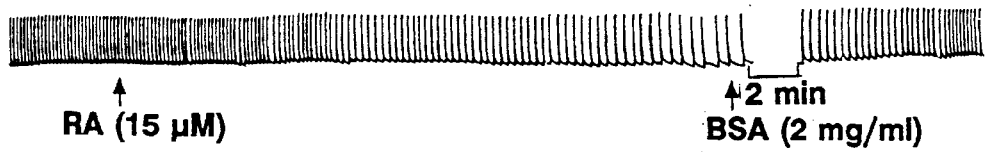
FIG. 1A is a chart recorder tracing showing the effect of all-trans-retinoic acid on the contraction amplitude and contraction rate of spontaneously beating, isolated, neonatal rat cardiomyocytes. Perfusion of the myocytes with 15 μM all-trans-retinoic acid reduced the beating rate within 2 minutes. Washing with bovine serum albumin (2 mg/ml) quickly reversed the effect.

The invention features a simple, rapid, and efficacious method for the prevention of a potentially lethal cardiac arrhythmia in a susceptible patient. In the method, all-trans-retinoic acid, or an active analog thereof, is used to achieve potent antiarrhythmic effects within minutes.

For convenience, the invention is described below in terms of retinoic acid. It should be appreciated, however, that the description applies generally to any active analog of retinoic acid, as well.

The invention can be used in an emergency situation to prevent an imminent potentially lethal cardiac arrhythmia, e.g., ventricular fibrillation, in a susceptible patient. Examples of emergency situations wherein a patient is susceptible to an imminent potentially lethal cardiac arrhythmia include the following: myocardial infarction, myocardial ischemia, anaphylactic shock, cardiac wounds or physical trauma, asphyxia (e.g., due to near-drowning, carbon monoxide poisoning, anesthesia, drug overdose), or overdose of a cardiac glycoside, catecholamine, or thyroxin.

Specific signs of imminent ventricular fibrillation include stuttering arrhythmia, bizarre electrocardiogram patterns, or a storm of premature heartbeats lasting more than about three seconds, especially when these signs are present in a patient exhibiting other signs or symptoms of myocardial infarction.

The invention can also be used prophylactically in a non-emergency clinical situation where a patient is known to be at increased risk of a potentially lethal cardiac arrhythmia. Examples of such non-emergency clinical situations include those where a patient: is experiencing angina pectoris, has had a previous myocardial infarction, has recently undergone open heart surgery, is undergoing treatment by electrical stimulation, or is undergoing treatment with a drug whose potential adverse side effects include cardiac arrhythmia.

A hospital surgical procedure may present a significant risk of ventricular fibrillation, e.g., where a patient has a history of myocardial infarction or other heart abnormality. Open heart surgery (e.g., coronary bypass grafting), generally presents an elevated risk of ventricular fibrillation. When a heart has been arrested by cooling and high potassium, there is a risk of ventricular fibrillation during rewarming of the heart and attempts to initiate normal heart beating. Where a surgical procedure presents a significant risk of a potentially lethal cardiac arrhythmia, intravenous infusion of retinoic acid can be initiated before or during surgery, to minimize the risk.

The present invention can be used for treatment of a patient diagnosed as having a recurrent arrhythmia. Such a recurrent arrhythmia can, but does not necessarily, result from a birth defect. A patient with a recurrent arrhythmia can be identified by electrocardiography, echocardiography, or other diagnostic methods. A patient with a recurrent arrhythmia can be symptomatic (e.g., intermittent chest pain) or asymptomatic.

Testing of the efficacy of a therapy selected for controlling an identified recurrent arrhythmia typically involves an invasive procedure similar to the following. A catheter containing an electrode is placed into the patient's heart. A clinician then applies a programmed electrical stimulation of the heart muscle, to elicit the suspected arrhythmia. Once the arrhythmia is induced, the heart is defibrillated. The clinician then chooses a medication for the patient. After the patient has received the chosen therapy for approximately 6 to 8 weeks, the clinician again performs the invasive electrostimulation test (above), and attempts to induce the previously observed arrhythmia. If the arrhythmia is not elicited by the electrostimulation, the therapy is continued. If the electrostimulation elicits the arrhythmia, the clinician prescribes an alternate drug therapy. The patient then undergoes the electrostimulation testing procedure again, 6 6 to 8 weeks thereafter. Alternatively, the patient undergoes implantation of an electronic defibrillator.

The method of this invention can be applied to avoid repetition of the invasive electrostimulation testing procedure. After the arrhythmia is initially induced by electrostimulation, and the patient's heart is defibrillated, an antiarrhythmic composition is administered according to the present invention. Because antiarrhythmic effects are achieved within minutes, the clinician can then immediately repeat the electrostimulation test to determine whether the composition tested is effective in preventing the arrhythmia in the patient being tested. The need for repeated invasive procedures is advantageously avoided, because the electrostimulation testing procedure is carried out using only a single catheterization.

Preferably, retinoic acid is administered as soon as a patient is identified as being at risk of an imminent potentially lethal cardiac arrhythmia. For example, intravenous infusion of retinoic acid can be initiated by a physician, nurse, or emergency medical technician at the scene of an emergency. The intravenous infusion can be continued until the patient is stabilized and appears no longer to be susceptible to an imminent potentially lethal cardiac arrhythmia.

A severe cardiac arrhythmia such as ventricular fibrillation can lead to brain damage or death within minutes. Therefore, whenever possible, the administration of retinoic acid according to this invention is accomplished before the onset of a potentially lethal cardiac arrhythmia. Alternatively, in an emergency situation, where a potentially lethal cardiac arrhythmia has already begun, retinoic acid can be administered to terminate the existing cardiac arrhythmia.

In the practice of this invention, retinoic acid can be administered by any route suitable for delivery to the myocardium. The preferred route is intravenous. In a particularly acute emergency, e.g., after the onset of ventricular fibrillation, the retinoic acid can be administered by bolus injection directly into the heart. Such direct injection is preferably followed by continous intravenous infusion.

Retinoic acid can be administered either as a free acid or as a pharmaceutically acceptable salt. Free retinoic acid is only sparingly soluble in water. Therefore, the practice of this invention will typically include a means for enhancing the aqueous solubility of retinoic acid. For example, retinoic acid can be emulsified, formulated with a suitable carrier, e.g., a transport protein, or converted to a suitable salt. In the preparation of such dosage forms, the retinoic acid is typically initially dissolved in a small volume of ethanol.

The preferred means for enhancing the aqueous solubility of retinoic acid is formulation with a transport protein, which binds to the retinoic acid. A preferred transport protein is delipidated human serum albumin. When human serum ablumin is used as a retinoic acid transport protein, the retinoic acid is preferably formulated with the human serum albumin at a ratio of approximately 5 molecules of retinoic acid per molecule of human serum albumin. In addition to enhancing the aqueous solubility of retinoic acid, a transport protein such as human serum albumin effectively reduces the exposure of erythrocyte membranes to free retinoic acid. This is advantageous because excessive exposure of erythrocyte membranes to free retinoic acid can cause hemolysis.

In an alternative formulation, the retinoic acid is emulsified. If an emulsion is used, it is preferably a phospholipid microsome emulsion. A phospholipid microsome emulsion is prepared using phosphotidyl choline, glycerol, water, and sonication, according to standard procedures.

Preferably, the total amount of retinoic acid used in a single emergency prevention of a potentially lethal arrythmia in a human patient is from 2 to 1,000 mg per kg total body weight. More preferably, the total amount is from 10 to 400 mg retinoic acid per kg body weight. The molar concentration of retinoic acid in the solution or emulsion administered can vary, depending on the total volume in which the retinoic acid is administered.

The initial dose, either by bolus injection or intravenous infusion, typically includes a predetermined amount of retinoic acid. In the practice of the invention, however, the total dosage can be "titrated" according to the patient's response. For example, if a first dose of retinoic acid is administered to a patient, and that patient proceeds to develop a potentially lethal arrhythmia, or exhibits signs or symptoms that such an arrhythmia is imminent, a second dose of retinoic acid can be administered. Clinical observation of the patient and assessment of the need for one or more additional doses of retinoic acid is within ordinary skill in the art.

Where the retinoic acid is administered prophylactically in a non-emergency situation, e.g., in preparation for heart surgery, it is preferably administered by intravenous infusion, rather than by bolus injection. The total dosage is preferably comparable to the dosage used in an emergency situation (above). The formulation, however, can optionally contain a relatively low concentration of retinoic acid, because the intravenous infusion can be administered over a longer time course.

EXPERIMENTAL INFORMATION

Cell Culture

Cardiac myocytes were isolated from 1 day old rats using the Neonatal Cardiomyocyte Isolation System (Worthington Biochemical Corp, N.J.), essentially according to the method of Toraason, et al (*Toxicology* 56:107 (1989)). In this method, the minced ventricular tissue is incubated overnight with trypsin in the cold. The isolated cells were placed on 15 mm glass coverslips in petri dishes and cultured at 37° C. in air with 5% $CO_2$ added and 98% relative humidity in a tissue culture incubator (Model 3123, Forma Scientific, Ohio). The culture medium was changed every other day. After 48 hours in culture, cells exhibited regular spontaneous contractions. Cells were used for experiments after 3–5 days of culture, at which time the culture was not confluent. Plating density ($3 \times 10^5$ cells/ml) is chosen to create clumps of syncytia comprised of 10 or more cells which contract spontaneously, rhythmically and in unison.

Measurement of Cell Contraction

Changes in amplitude of contraction and beating rate of cultured cardiomyocytes were determined using a phase contrast microscope and video-monitor edge-detector essentially as described by Barry et al. (*J. Mol. Cell Cardiol.* 16:155 (1984)). A glass coverslip with attached cultured myocytes was placed in a chamber continuously perfused during contractility measurements with a Hepes buffered saline solution (140 mM NaCl, 5 mM KCl, 1.0 $MgCl_2$, 1.2 mM $CaCl_2$, 1.0 mM $Na_2HPO_4$, 5.0 mM Hepes, and 10 mM glucose, pH adjusted to 7.4 with NaOH). The chamber was placed on the stage of a Zeiss Axiovert 10 inverted microscope which was enclosed by a temperature controlled, Lucite box heated to 37° C. The inlet to the perfusion system was connected by a 4-way manifold with polyethylene tubing connecting to two syringe pumps (Harvard Apparatus Inc., South Natick, Mass.) so that the coverslip could be superfused sequentially with different solutions. The flow rate was 20 ml/hr. The cells were magnified with a 32X objective. Plastic microspheres (2–3 μm diameter) were added to the culture on day 2, to provide an improved image for measurement of myocyte motion. The image was monitored with a CCD video camera (Javelin Electronics, Las Angeles, Calif.) attached to the microscope observation port and displayed on a television screen. Motion along a selected raster line segment was quantified by a video motion detector system (Barry et al., supra). Although the motion of a single cell was monitored, that cell was one in a syncytium comprised of 10 or more cells contracting at the same rate. Motion signals were recorded until a 5–10 minute stable baseline during superfusion with normal Hepes-buffered solution was achieved. Perfusion with various test solutions was then carried out. Motion signals were recorded using a Panasonic AG-1960 tape recorder and a Grass 79D strip chart recorder (Grass Instrument Co., Quincy, Mass.).

Animal Experiments

To determine the efficacy of the protective effect of retinoic acid on arrhythmias induced by ischemia-reperfusion, twenty day-old Sprague-Dawley rats weighing 400–500 gm were subjected to experimental acute myocardial ischemia by surgical occlusion of coronary vessels. This preparation has been extensively used for the production of ischemia, arrhythmias and infarction and for the assessment of antiarrhythmic therapies (see, e.g., McLennan et al., supra; Selye et al., *Angiology* 11:398 (1960); Kane et al., *Br. J. Pharmacol.* 82:349 (1984); Curtis et al., *J. Mol. Cell Cardiol.* 19:339 (1987)). The rats were anesthetized with pentobarbital sodium (60 mg/kg intraperitoneally), intubated and ventilated with room air by a constant volume-cycled respirator (Harvard Apparatus, South Natick, Mass.). An intravenous catheter (22 GA) connected to a syringe pump (Harvard Apparatus Inc. Mass.) was inserted into the right external jugular vein and used to infuse normal saline or the retinoic acid emulsion. The chest was opened by left thoracotomy. The pericardium was opened and the heart was exteriorized. A 6-0 polypropylene suture attached to a 13 mm taper needle was placed around the left anterior descending coronary artery near its origin. The heart was then repositioned in the thoracic cavity. Occlusion and reperfusion of the artery were achieved by tightening and releasing the suture.

Fifteen minutes after the surgical procedures, the hearts were perfused with 5 ml of either normal saline (as control) or retinoic acid solution (containing 1.5 mg all-trans-retinoic acid (1mM), 100 mg BSA (0.3 mM)) at a rate of 8 ml/h. Following the perfusion, occlusion of the artery was started and lasted for 15 min. The electrocardiogram ("ECG") was recorded using a HP 1500A Electrocardiograph and a Del Mar Avionics' Model 445 Electrocardiocorder Recorder throughout the duration of occlusion and a 10 minute period of reperfusion. Ventricular tachycardia ("VT") was identified as four or more consecutive beats of similar morphology with no preceding P wave, having a basic cycle length at least 20% less than that of prevailing complexes. Ventricular fibrillation ("VF") was identified by chaotic electrical activity. No attempt was made artificially to revert episodes of VT or VF. Arrhythmias were assessed during occlusion and reperfusion by counting the number of ventricular extra beats ("VEBs") and the incidence and total duration of all episodes of VT and VF. In addition, severity of arrhythmias was assessed quantitatively by an arrhythmia score as described by McLennan et al (*Am. Heart J.* 16:709 (1988)).

Materials

Neonatal Cardiomyocyte Isolation System Kit was purchased from Worthington Biochemical Corp., New Jersey. All-trans-retinoic acid, 13-cis-retinoic acid, retinol, retinal, lysophosphatidylcholine and fatty acid-free bovine serum albumin were obtained from Sigma Chemical Co., St Louis, Mo. Isoproterenol was obtained from Elkins-Sinn, Inc., Cherry Hill, N.J. Retinoic acid was dissolved weekly in ethanol at a concentration of $10^{-2}M$ and stored under a nitrogen atmosphere at $-20°$ C. The final concentration of ethanol was negligible and had no effect on myocyte contraction. retinoic acid (1 mM) infusion solution was made by dissolving 1.5 mg retinoic acid in 100 μl ethanol, transferring to 5 ml saline containing 100 mg BSA, and vortexing or sonicating for 2 minutes.

Statistics

Student's t test was used for comparisons between control and experimental groups with P<0.05 considered significant. Results are presented as mean ±SE.

Effects of Retinoic Acid on Contraction of Myocytes

To test the effects of retinoic acid on contraction of cultured myocytes, retinoic acid was added to the perfusion solution. After an initial control recording was obtained during perfusion with Hepes-buffered saline solution, the superfusate was switched to Hepes-buffered saline solution containing 10–20 μM all-trans-retinoic acid. Within 2–3 minutes after exposure to RA, a gradual slowing of the beating rate with no change in the amplitude of contraction occurred (n=10). The reduction in the beating rate could be reversed within 5–10 minutes when the superfusate was returned to the original solution, in some case, within 3–5 minutes, when delipidated bovine serum albumin ("BSA," 2 mg/ml) was added.

A representative example of the effect of retinoic acid is shown in FIG. 1A. The effects of other retinoids including all-trans-retinol (vitamin A), all-trans-retinal and 13-cis-retinoic acid (13-cis-RA) were also tested. Both retinol and retinal at even higher concentrations (30–50 μM) did not have similar effects during a 30 minute perfusion (n=5, FIG. 1B and 1C). However, 13-cis-retinoic acid exhibited two-phase effects: an initial slowing of the beating rate for 3–5 minutes followed by irregular, rapid beating with a progressive reduction in the amplitude of contraction (n=6, FIG. 1D). The effects of the retinoids on the rate and amplitude of contraction of cultured myocytes is are summarized in Table 1. Other fat-soluble vitamins, including vitamins D, E and K displayed no effect on the rate or amplitude of contraction of cultured myocytes (data not shown).

TABLE 1

Effects of retinoids on beating rate and amplitude of contractions of cultured neonatal rat cardiac myocytes

| Retinoids | Rate (% of control) | | Amplitude (% of control) | |
| --- | --- | --- | --- | --- |
| | 5 min | 10 min | 5 min | 10 min |
| All-trans-RA (15 μM, n = 10) | $54.3 \pm 2.1^a$ | $27.6 \pm 1.9^a$ | $101.0 \pm 1.5$ | $102.5 \pm 0.9$ |
| Retinol (30 μM, n = 5) | $96.5 \pm 2.5$ | $97.7 \pm 1.5$ | $98.2 \pm 1.0$ | $99.3 \pm 3.0$ |
| Retinal (30 μM, n = 5 | $100.0 \pm 4.0$ | $99.5 \pm 3.2$ | $98.3 \pm 1.7$ | $99.0 \pm 1.5$ |
| 13-cis-RA (15 μM, n = 6) | $48.8 \pm 5.2^a$ | $83.0 \pm 10.1^b$ | $85.0 \pm 9.0^b$ | $15.0 \pm 4.5^a$ |

RA = retinoic acid
$^a p < 0.001$
$^b p < 0.05$

In the experiments whose results are summarized in Table 1, spontaneous beating rates of the myocytes were measured for a 1-minute control period before addition of the retinoid, and then at 5 and 10 minutes after addition of the retinoids. Because of the significant variation in the control beating rates of different myocytes, we the normalized values obtained after addition of the retinoids to the percentage of the control beating rate and compared that value with the control expressed as 100% of the control beating rate. Paired "before" and "after" measurements were made on the same myocyte. Numerical values in Table 1 are means ±SEM.

Figure 2A:
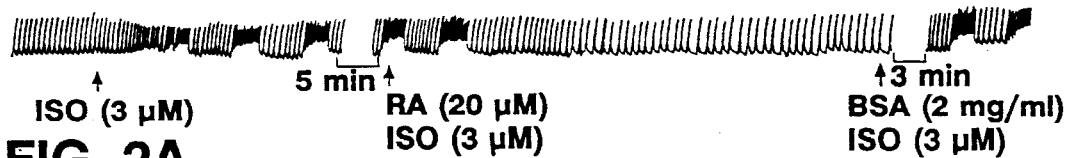
FIG. 2A is a chart recorder tracing showing the protective effects of all-trans-retinoic acid on tachyarrhythmias induced in cultured myocytes by isoproterenol ("ISO"). Perfusion of the cells with 3 μM ISO induced repetitive, intermittent contractures of the myocytes. Addition of 20 μM all-trans-retinoic acid terminated the contractures/tachyarrhythmias. Subsequent perfusion of the cells with retinoic acid-free medium containing ISO and bovine serum albumin reinstated the contractures.
Figure 2B:
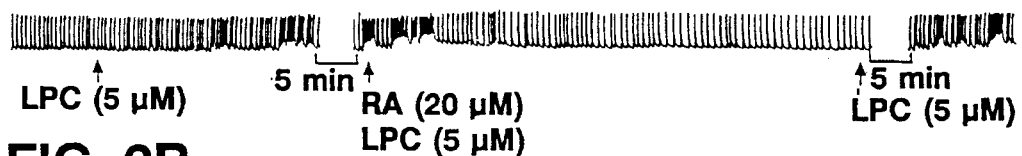
FIG. 2B is a chart recorder tracing showing the protective effects of all-trans-retinoic acid on tachyarrhythmias induced in cultured myocytes by lysophosphatidylcholine ("LPC"). Perfusion of the cells with 5 μM LPC induced repetitive, intermittent contractures of the myocytes. Addition of 20 μM all-trans-retinoic acid terminated the contractures/tachyarrhythmias. Subsequent perfusion of the cells with retinoic acid-free medium containing LPC and bovine serum albumin reinstated the contractures.
Figure 2C:
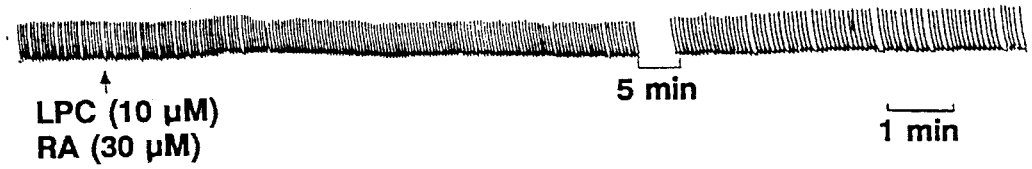
FIG. 2C is a chart recorder tracing showing that simultaneous addition of 30 μM all-trans-retinoic acid and 10 μM LPC caused no contractures, but reduced the beating rate.

Effects of Retinoic Acid on Isoproterenol or Lysophosphatidylcholine-Induced Arrhythmias To test the antiarrhythmic effects of retinoic acid in cultured cell preparations, tachyarrhythmias were induced by perfusion of the myocytes with either 3 μM isoproterenol ("ISO") or 5 μM lysophosphatidylcholine ("LPC"), and then retinoic acid (20 μM) was subsequently added to the medium. Table 2 summarizes the effects of all-trans-retinoic acid on isoproterenol or lysophosphatidylcholine-induced arrhythmias. Representative recordings of these experiments are shown in FIGS. 2A–2C. Within 3 min after addition of 20 μM retinoic acid, the cell contractures/tachyarrhythmias caused by 3 μM ISO were terminated followed by a reduction in the beating rate (n=7). When the superfusate was changed to the medium containing 3 μM ISO plus BSA (2 mg/ml) but no RA, three minutes later, the contraction rate increased and then the tachyarrhythmias recurred (FIG. 2A). Similarly, after induction of similar tachyarrhythmias by 5 μM LPC, addition of retinoic acid (20 μM) stopped the arryhthmias within 3–5 minutes (n=9). When the superfusate was switched back to the medium containing 5 μM LPC alone, the arrhythmias recurred after 5 min of further perfusion (FIG. 2B). Alternatively, retinoic acid also could prevent the tachyarrhythmias since simultaneous addition of retinoic "acid (30 μM) and LPC (10 μM) produced no tachyarrhythmia/contracture (FIG. 2C; n=3). In contrast, retinol, retinal and 13-cis-retinoic acid did not protect the cells against the arrhythmias. In some cases, 13-cis-RA even worsened the arrhythmias.

TABLE 2

Effects of all-trans-RA on the occurrence of tachyarrhythmias induced by ISO, LPC, or LPC plus RA in cultured neonatal rat ventricular myocytes

| | Tachyarrhythmia (contracture) | | | |
|---|---|---|---|---|
| | Before RA | | 5 min after RA (20 μM) | |
| | No. of events | Total duration (min) | No. of events | Total duration (min) |
| ISO (n = 7) | $7.3 \pm 0.7^a$ | $2.1 \pm 0.2^a$ | 0 | 0 |
| LPC (n = 9) | $7.8 \pm 0.9^a$ | $2.5 \pm 0.3^a$ | 0 | 0 |
| LPC + RA (n = 3) | 0 | 0 | — | — |

ISO = isoproterenol
LPC = lysophosphatidyl choline
RA = retinoic acid
$^a p < 0.001$ In the experiments whose results are summarized in Table 2, the number of repetitive, intermittent tachyarrhythmic events occurring in a 5-minute control period before addition of retinoic acid was comparable to the number of events occurring during a 5-minute period beginning 5 minutes after addition of retinoic acid. The "total duration" is the sum of the duration of each of the events during the respective 5-minute periods. During the 5-minute period starting 5 minutes after addition of retinoic acid, there were no events in the ISO and LPC experiments since retinoic acid terminated all the tachyarrhythmias by 5 minutes after its addition, whereas addition of LPC and retinoic acid added simultaneously prevented induction of any tachyarrhythmia.

Effects of Retinoic Acid on Ischemia and Reperfusion-Induced Arrhythmias

Figure 3A:
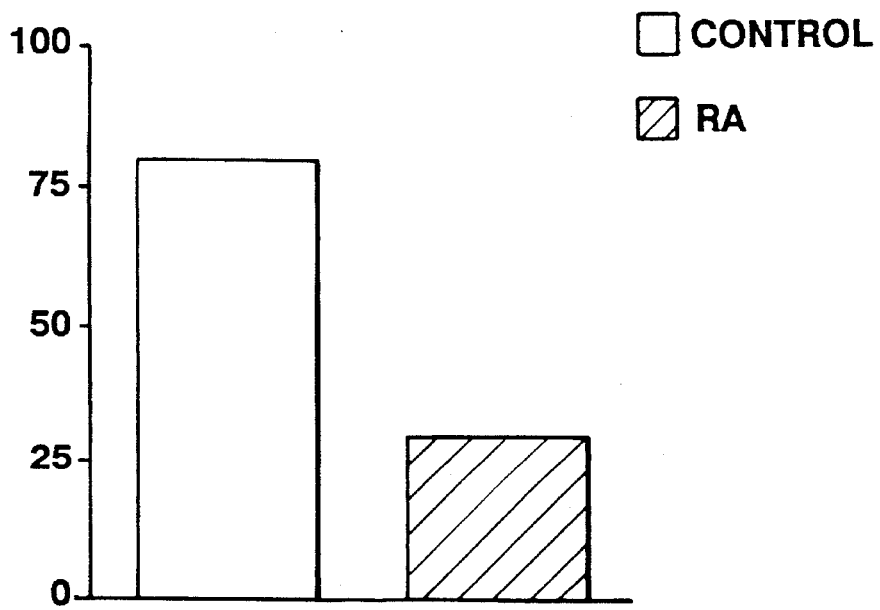
FIG. 3A is a bar graph showing the effect of all-trans-retinoic acid on ischemia- and reperfusion-induced arrhythmias, in terms of percentage of incidence of ventricular fibrillation during 15-minute ischemia and 10-minute reperfusion periods, in rats with or without infusion of all-trans-retinoic acid. Light bar represents control treatment; dark bar represents retinoic acid treatment.
Figure 3B:
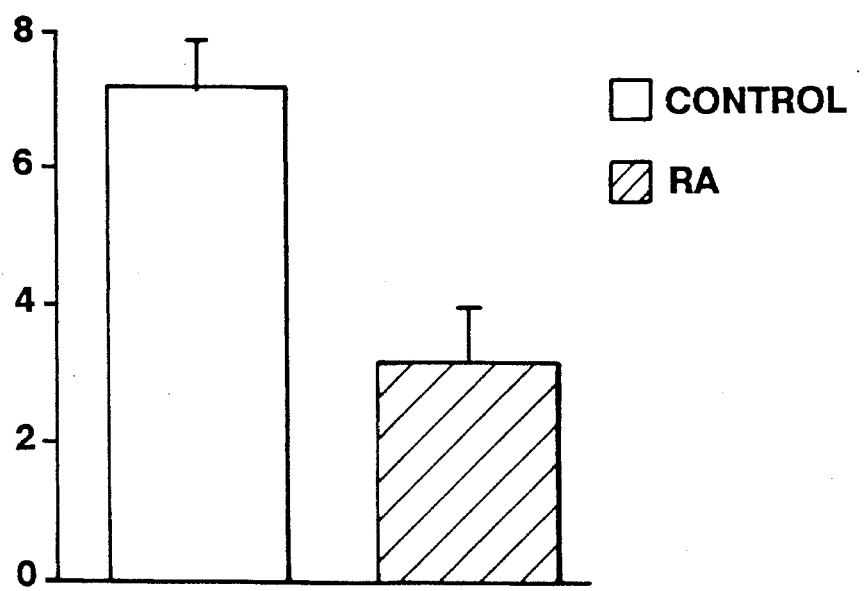
FIG. 3B is a bar graph showing the effect of all-trans-retinoic acid on ischemia- and reperfusion-induced arrhythmias, in terms of arrhythmia score. The arrhymia score was calculated using a 0–9 scale similar to that of McLennan et al. (Am. Heart J. 16:709 (1988)). Light bar represents control treatment; dark bar represents retinoic acid treatment. In both treatments, n=10; * indicates p<0.01.

To determine the efficacy of the protective effects of all-trans-retinoic acid against ischemia-induced arrhythmias in whole animals, the incidence and severity of ventricular arrhythmias were assessed during 15 min of coronary artery occlusion and 10 min of reperfusion in adult rats with or without prior intravenous infusion of all-trans-retinoic acid (1.5 mg). FIG. 3A shows the percent incidence of ventricular fibrillation in both control and retinoic acid infused groups. The incidence of ventricular fibrillation was significantly lower in rats infused with retinoic acid when compared with control rats (8 of 10 animals in the control group developed VF while only 3 of 10 rats in the retinoic acid treated group had VF). Five of the 8 animals in the control group developed VF during the period of occlusion and died of the sustained VF. The VF observed in the 3 animals infused with retinoic acid occurred during reperfusion and terminated spontaneously. Six animals with no VF in the retinoic acid group showed a reduction in heart rate by 10–15% after administration of RA. In addition, when the incidence, number, and duration of the arrhythmias were taken into account using an arrhythmia scoring scale (McLennan et al., supra), the retinoic acid-infused rats had a significantly lower arrhythmia score compared with the control group, thus indicating an overall reduction in arrhythmic vulnerability (FIG. 3B).

Figure 1B:
FIG. 1B is a chart recorder tracing showing that perfusion with 30 μM all-trans-retinol had no effect on the contraction amplitude or contraction rate of spontaneously beating, isolated, neonatal rat cardiomyocytes.
Figure 1C:
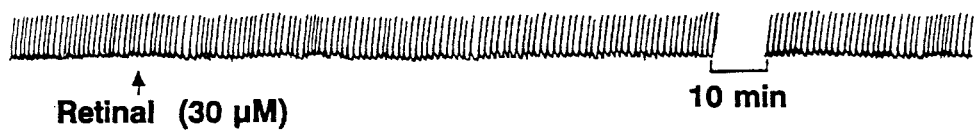
FIG. 1C is a chart recorder tracing showing that perfusion with 30 μM all-trans-retinal had no effect on the contraction amplitude or contraction rate of spontaneously beating, isolated, neonatal rat cardiomyocytes.

Retinoids (retinoic acid, retinol and retinal) in the form of acid, alcohol or aldehyde were tested. As shown in FIG. 1A, retinoic acid displayed antiarrhythmic activity, but retinol and retinal did not (FIGS. 1B and 1C). This suggested that the free carboxyl group was essential for antiarrhythmic activity. Perfusion with delipidated BSA, which can bind retinoic acid (Smith et al., *Biochem. J.* 132:821 (1973)), reversed the protective action of retinoic acid. This indicates that retinoic acid's antiarrhythmic action does not require covalent linkage to phoshpolipids or other molecules in the cell membranes.

Retinoic acid exerts effects on cell growth and differentiation by binding to the nuclear receptors that activate transcription of a number of genes (see, e.g., DeLuca, *FASEB J.* 5:2924 (1991)). This known mechanism of action of retinoic acid does not account for the antiarrhythmic effects of retinoic acid in the present invention, because the onset and reversal of the antiarrhythmic effects occur within minutes. It is likely that retinoic acid itself acts on cell membrane components by partition into lipid bilayer. Partition of free retinoic acid into membrane lipid may modify the conformation of membrane-bound proteins and thereby change their function through direct interaction with the proteins or perturbation of the lipid environment around the proteins. Inhibition of automaticity/excitability may result from effects of retinoic acid on membrane ion channels, leading to a reduction in cell beating rate and heart rate.

The decreased excitability of the cardiac cells makes them less prone to respond to aberrant electrical impulses and chemical arrhythmogenic agents that might occur during myocardial ischemia or reperfusion. As shown in FIGS. 2A and 2B, all-trans-retinoic acid can effectively prevent and terminate the arrhythmias induced by ISO and LPC, two important arrhythmogenic mediators in the ischemic heart (*Cardiovasc. Res.* 27:703 (1993)). These mediators that have been shown to increase automaticity (Podrid et al., *Circulation* 82 (suppl I):I103–13 (1990); Duan et al., *Eur. J. Pharmacol.* 192:355 (1991)). The all-trans-retinoic acid significantly reduced both the incidence and severity of VT and VF induced by ischemia or reperfusion in the whole animals.

Figure 1D:
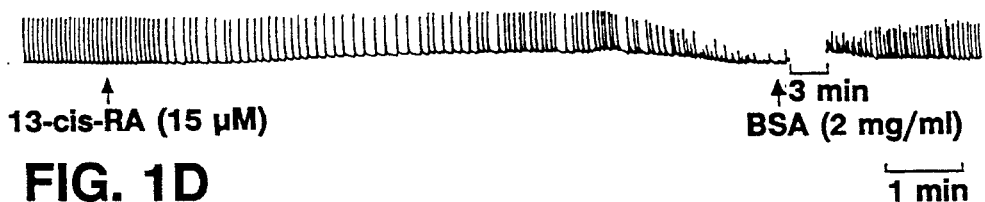
FIG. 1D is a chart recorder tracing showing that perfusion with 15 μM 13-cis-retinoic acid resulted in a slowing of the beating rate for a few minutes, followed by chaotic beating with a reduction in contractility. Washing with bovine serum albumin (2 mg/ml) reversed the effect.

The effect of 13-cis-retinoic acid on myocyte contraction is significantly different from the effect of all-trans-retinoic acid. The second phase effect of its action during which chaotic beating occurs (as shown in. FIG. 1D) seems a likely explanation for its failure to protect the cell against tachyarrhythmias. The chaotic beating induced by 13-cis-retinoic acid may be a result of uncoupling of the cells since 16-doxylstearic acid, which uncouples gap junctions in rat heart cells (Burt, *Am. J. Physiol.* 256:C913 (1989)), produces similar effects on the contraction of the cultured myocytes (data not shown).

Other embodiments are within the following claims.

We claim:

1. A method for terminating an existing potentially lethal cardiac arrhythmia, or preventing an imminent potentially lethal cardiac arrhythmia, said method comprising administering a composition comprising an effective amount of antiarrhythmic compound defined by the formula:

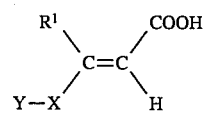

wherein X is selected from the group consisting of:

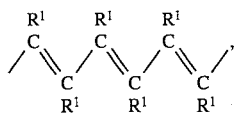

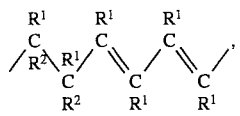

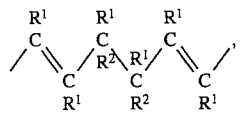

and

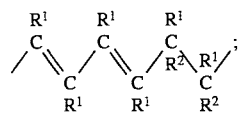

Y is selected from the group consisting of:

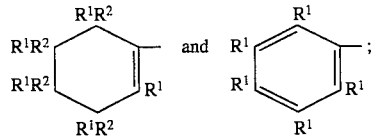

$R^1$ is selected from the group consisting of H, methyl, and ethyl; and $R^2$ is selected from the group consisting of H, methyl, and ethyl.

2. The method of claim 1, wherein said antiarrhythmic compound is all-trans-retinoic acid.

3. The method of claim 1, wherein said potentially lethal cardiac arrythmia is ventricular fibrillation.

4. The method of claim 1, wherein said potentially lethal cardiac arrythmia is ventricular tachycardia.

5. The method of claim 1, wherein said effective amount of said antiarrhythmic compound is between 2 and 1,000 mg per kg total body weight.

6. The method of claim 5, wherein said effective amount of said antiarrhythmic compound is between 10 and 400 mg per kg total body weight.

7. The method of claim 1, wherein said composition is administered by intravenous infusion.

8. The method of claim 1, wherein said composition is administered by bolus injection.

9. The method of claim 8, wherein said bolus injection is intracardial.

10. The method of claim 1, wherein said composition comprises a transport protein suitable for serum transport of said antiarrythmic compound.

11. The method of claim 10, wherein said transport protein is human serum albumin.

12. The method of claim 11, wherein the molar ratio of said antiarrhythmic compound to said human serum albumin is from 1 to 7.

13. The method of claim 12, wherein said molar ratio is approximately 5.

* * * * *